(12) United States Patent
van Niekerk (10) Patent No.: US 10,674,932 B2
(45) Date of Patent: Jun. 9, 2020

(54) ORIENTATION TRACKING DEVICE FOR MRI

(71) Applicant: University of Cape Town, Rondebosch, Cape Town (ZA)

(72) Inventor: Adam Marthinus Johannes van Niekerk, Claremont (ZA)

(73) Assignee: University of Cape Town, Cape Town (ZA)

( * ) Notice: Subject to any disclaimer, the term of this patent is extended or adjusted under 35 U.S.C. 154(b) by 158 days.

(21) Appl. No.: 15/739,422

(22) PCT Filed: Jul. 14, 2016

(86) PCT No.: PCT/IB2016/054209
§ 371 (c)(1),
(2) Date: Dec. 22, 2017

(87) PCT Pub. No.: WO2017/021804
PCT Pub. Date: Feb. 9, 2017

(65) Prior Publication Data
US 2018/0184940 A1 Jul. 5, 2018

(30) Foreign Application Priority Data
Jul. 31, 2015 (GB) .................................. 1513558.5

(51) Int. Cl.
*G01R 33/28* (2006.01)
*A61B 5/055* (2006.01)
(Continued)

(52) U.S. Cl.
CPC .............. *A61B 5/055* (2013.01); *A61B 5/067* (2013.01); *A61B 5/721* (2013.01); *G01R 33/28* (2013.01);
(Continued)

(58) Field of Classification Search
CPC ............ G01R 33/4816; G01R 33/4818; G01R 33/482; G01R 33/4822; G01R 33/4824;
(Continued)

(56) References Cited

U.S. PATENT DOCUMENTS

2003/0184297 A1 10/2003 Jakab
2005/0107685 A1 5/2005 Seeber
(Continued)

FOREIGN PATENT DOCUMENTS

WO 2014/150961 A1 9/2014

OTHER PUBLICATIONS

International Search Report of the International Searching Authority dated Sep. 23, 2016, issued in connection with International Application No. PCT/IB2016/054209 (3 pages).
(Continued)

*Primary Examiner* — Tung X Nguyen
(74) *Attorney, Agent, or Firm* — McCarter & English, LLP (57) ABSTRACT

An orientation tracking device includes a memory for storing data including magnetic reference data relating to the direction of a static magnetic field of a magnetic imaging scanner in a selected principle co-ordinate frame and earth gravitational reference data relating to the direction of the gravitational field of the earth in the principle co-ordinate frame. The device also includes an accelerometer, magnetometer and communication module. A processor is adapted for receiving from the magnetometer measured magnetic field vector and from the accelerometer a measured acceleration vector. These vectors are in a co-ordinate frame of the orientation tracking device, within the magnetic imaging scanner in which the orientation tracking device is placed in use. The processor then determines the orientation of the device with respect to the principle co-ordinate frame by
(Continued)

comparing the measured vectors from the accelerometer and magnetometer with the stored gravitational reference data and magnetic reference data respectively.

15 Claims, 8 Drawing Sheets (51) Int. Cl.
    *A61B 5/06*     (2006.01)
    *A61B 5/00*     (2006.01)
    *G01R 33/565*     (2006.01)

(52) U.S. Cl.
    CPC   *A61B 2562/0223* (2013.01); *G01R 33/56509* (2013.01)

(58) Field of Classification Search
    CPC ............ G01R 33/4826; G01R 33/4828; G01R 33/483; G01R 33/4831; G01R 33/4833; G01R 33/4835; G01R 33/4836; G01R 33/4838; G01R 33/50; G01R 33/543; G01R 33/5602; G01R 33/5604; G01R 33/5605; G01R 33/5607; G01R 33/5608; G01R 33/561; G01R 33/5611; G01R 33/5612; G01R 33/5613; G01R 33/5614; G01R 33/5615; G01R 33/5616; G01R 33/5617; G01R 33/5618; G01R 33/5619; G01R 33/563; G01R 33/56308

See application file for complete search history.

(56) References Cited

U.S. PATENT DOCUMENTS

| | | | |
|---|---|---|---|
| 2014/0077811 A1 | 3/2014 | Lin et al. | |
| 2016/0011022 A1* | 1/2016 | Zheng | G01R 33/00 702/94 |
| 2017/0089706 A1* | 3/2017 | Ribeiro | G01C 21/20 |
| 2017/0160086 A1* | 6/2017 | Kesaniemi | G01C 17/28 |

OTHER PUBLICATIONS

Written Opinion of the International Searching Authority dated Sep. 23, 2016, issued in connection with International Application No. PCT/IB2016/054209 (5 pages).

* cited by examiner

ORIENTATION TRACKING DEVICE FOR MRI

RELATED APPLICATIONS

This application is a U.S. National Phase Application under 35 U.S.C. 371 of International Application No. PCT/IB2016/054209 filed Jul. 14, 2016, which claims the benefit of United Kingdom Patent Application No. 1513558.5 filed on Jul. 31, 2015. The disclosures of these applications are incorporated herein by reference in their entireties.

BACKGROUND OF THE INVENTION

The present application relates to an orientation tracking device particularly for use with a Magnetic Resonance Imaging (MRI) scanner.

MRI scanners are most frequently used in medical environments to scan patients. However, any movement of the patient during the scanning process results in inaccuracies in the resulting scan.

It will be appreciated that patient movement is difficult to avoid, either simply because of the patient breathing or in longer scans it may become difficult for the patient to keep still. In addition, the patient may have a disease like Parkinsons which makes it physically impossible for them to keep still.

With modern MRI scanners now capable of sub-millimeter resolution imaging, involuntary motion is becoming a limiting factor in obtainable image clarity.

A method is required for detecting these movements so they can be compensated for in the scanning process.

The present invention provides a device and method to address this.

SUMMARY OF THE INVENTION

According to one example embodiment there is provided an orientation tracking device, the device including:
- a memory for storing data therein including magnetic reference data relating to the direction of a static magnetic field of a magnetic imaging scanner in a selected principle co-ordinate frame and earth gravitational reference data relating to the direction of the gravitational field of the earth in the principle co-ordinate frame;
- an accelerometer;
- a magnetometer;
- a communication module; and
- a processor connected to the accelerometer, the magnetometer and communication module, the processor adapted for:
  receiving from the magnetometer a measurement of a magnetic field vector in a co-ordinate frame of the orientation tracking device, within the magnetic imaging scanner in which the orientation tracking device is placed in use;
  receiving from the accelerometer a measurement of an acceleration vector in the orientation tracking device's co-ordinate frame, within the magnetic imaging scanner in which the orientation tracking device is placed in use; and
  determining the orientation of the device with respect to the principle co-ordinate frame by comparing the measured vectors from the accelerometer and magnetometer with the stored gravitational reference data and magnetic reference data respectively.

The processor typically receives further measurements from the accelerometer and magnetometer and uses these to determine the orientation of the device and wherein the processor compares the determined orientation of the device with a previously determined orientation of the device to quantify a change in orientation of a rigid object within the MRI scanner to which the device is attached, in use.

In a preferred example embodiment, the processor further applies filtering techniques to mitigate the effects of spurious readings.

The device may include at least one gyroscope also connected to the processor, so that the processor additionally uses measurements received from the gyroscope to determine orientation of the device.

The communication module additionally further feeds back acceleration and/or gyroscope measurements to the scanner for use to estimate future states of the device.

The device typically includes a battery to power the other components of the device wherein the battery is connected to the processor via a voltage regulator.

According to another example embodiment there is provided a method of using an orientation tracking device to track orientation, the method including:
- storing data including magnetic reference data relating to the direction of a static magnetic field of a magnetic imaging scanner in a selected principle co-ordinate frame and earth gravitational reference data relating to the direction of the gravitational field of the earth in the principle co-ordinate frame;
- receiving from a magnetometer a measurement of a magnetic field vector in a co-ordinate frame of the orientation tracking device, within the magnetic imaging scanner in which the orientation tracking device is placed in use;
- receiving from an accelerometer a measurement of an acceleration vector in the orientation tracking device's co-ordinate frame within the magnetic imaging scanner in which the orientation tracking device is placed in use; and
- determining the orientation of the device with respect to the principle co-ordinate frame by comparing the measured vectors from the accelerometer and magnetometer with the stored gravitational reference data and magnetic reference data respectively.

Typically, measurements are received periodically and used to determine the orientation of the device wherein the determined orientation of the device is compared with a previously determined orientation of the device to quantify a change in orientation of a rigid object within the MRI scanner to which the device is attached, in use.

Filtering techniques are preferably applied to mitigate the effects of spurious readings.

The method may further include receiving measurements from at least one gyroscope and additionally using the measurements received from the gyroscope to determine orientation of the device.

In addition, acceleration and/or gyroscope measurements may be fed back to the scanner for use to estimate future states of the device.

In a preferred embodiment, the principle co-ordinate frame is the co-ordinate frame of the MRI scanner.

Additionally, the reference data may be synthesised based on knowledge of the MRI scanner construction.

Furthermore, a change in orientation of a rigid object to which the device is connected in use may be used to predict the translation of that object.

DESCRIPTION OF EMBODIMENTS

An orientation tracking device particularly for use with a Magnetic Resonance Imaging (MRI) scanner is described below.

An MRI scanner is comprised of a super conducting magnet, radio frequency coils and gradient coils. The gradient coils are comprised of three separate coils that can spatially encode the physical space within the scanner bore in 3 orthogonal directions. At the iso-center of the MRI scanner the gradients coils have no effect on the magnitude of the magnetic field. This point cannot be modified or changed and is fixed for the specific MRI scanner. It is therefore physically impossible for one to rotate the encoded magnitude of the magnetic field about any point in physical space other than the gradient iso-center. Translational shifts are achieved by modifying the interpretation of the MR signal, and not through physical shifts in the constant magnitude of the static field.

It is because of this that real time feedback of orientation is vitally important as its effects on the MR signal are more complex than translational shifts. Orientation corrections need to be fed back immediately whilst translational motion can be corrected for retrospectively as long as it is accurately quantified.

Figure 2:
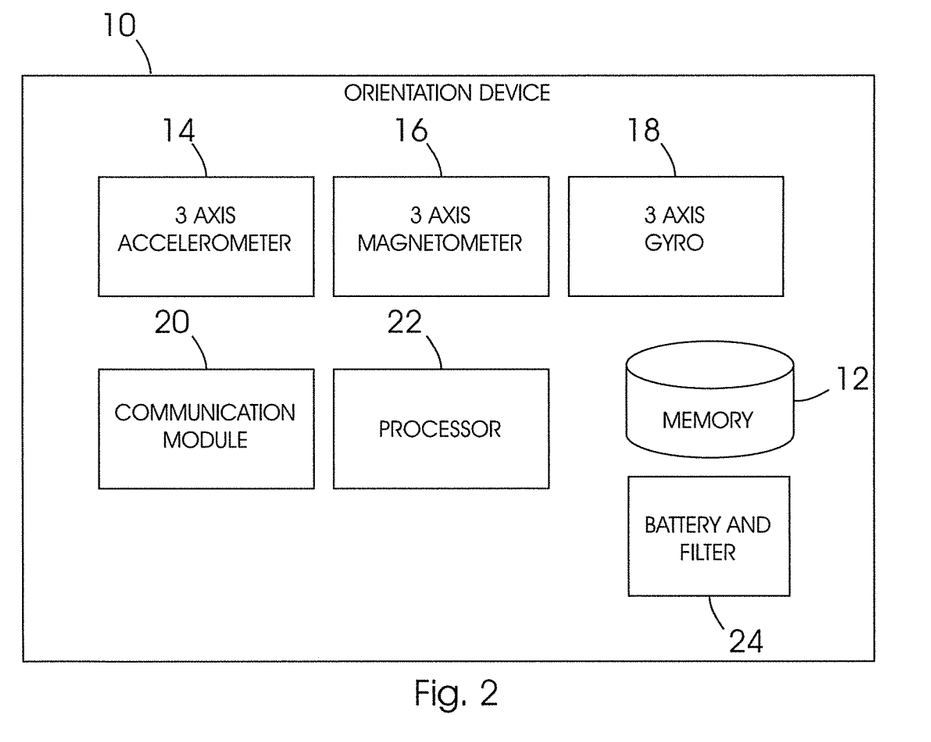
FIG. 2 is a block diagram illustrating an example device according to the present invention.
Figure 3:
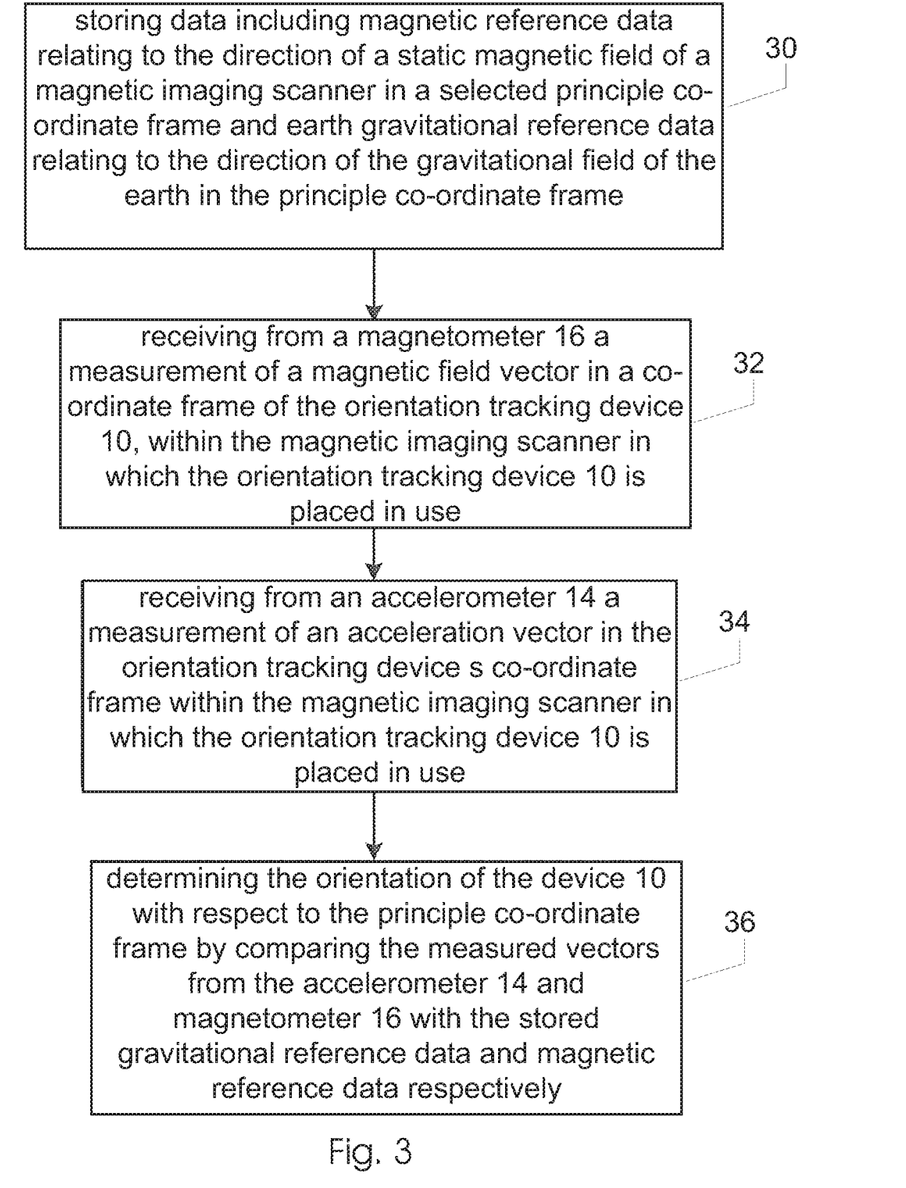
FIG. 3 is a block diagram illustrating method steps carried out by the device of FIG. 2.

Referring to the accompanying Figures, an orientation tracking device 10 includes a memory 12 for storing data therein including magnetic reference data relating to a static magnetic field of a magnetic imaging scanner and earth gravitational reference data relating to the gravitational field of the earth. FIG. 3, Step 30. These reference data define an initial principle co-ordinate frame.

In this regard, Magnetic Resonance Imaging relies on a highly homogeneous magnetic field for image acquisition. Even small fluctuations in this field will offset the precession frequency of the hydrogen atoms causing artefacts in the image. The gradient fields used for image space encoding are in the region of 40 mT/m for a 3 Tesla scanner. To encode anatomical features of around 1 mm size, the magnetic fields within the scanner need to be stable to well within 0.04 mT (typically specified in parts per million). This is many orders of magnitude smaller than the static field, showing how stable this field is required to be for image reconstruction.

As far as vector observations go, the static field within an MRI scanner (~$B_0$ field) is close to perfect for orientation estimates. It is highly independent of motion and is a fully defined in image space.

Even the relatively small magnitude gradient fields which encode image space have magnetic field vectors that point in the same direction (theoretically have no effect on the direction of the ~$B_0$ field). In the MRI scanner's construction it is beneficial to align the gradient coils to the static magnetic field to maximise their encoding effect. These properties allow the synthesis of the reference direction of the static magnetic field in the scanner's imaging reference frame to a relatively high degree of accuracy (less than 1 degree in an example MRI scanner). This is useful in the application of prospective motion correction; where orientation estimates are required with respect to the MRI scanner's co-ordinate frame.

In order to fully define an orientation within the MRI scanner bore, another vector observation is required. The second vector can't be parallel or anti-parallel to the first vector. Rather, the closer to orthogonal the second vector is to the first vector, the less vulnerable to noise an orientation estimate will be.

Due to structural and comfort reasons most MRI scanners image patients in the supine position. The MRI scanner's bore axis therefore lies parallel to the floor to accommodate the patient lying down. It is of interest to ensure the patient bed and imaging frame are aligned such that the images appear as expected to the radiographer. One can also appreciate that gravity levels are used as a reference in scanner construction. We can therefore synthesise a reference direction of gravity such that it runs parallel with the vertical axis of the imaging frame.

In this layout the earth's gravitational field vector is close to perfectly orthogonal to the static magnetic field of the scanner (within 0.1 degrees in one measured example MRI scanner).

Figure 1:
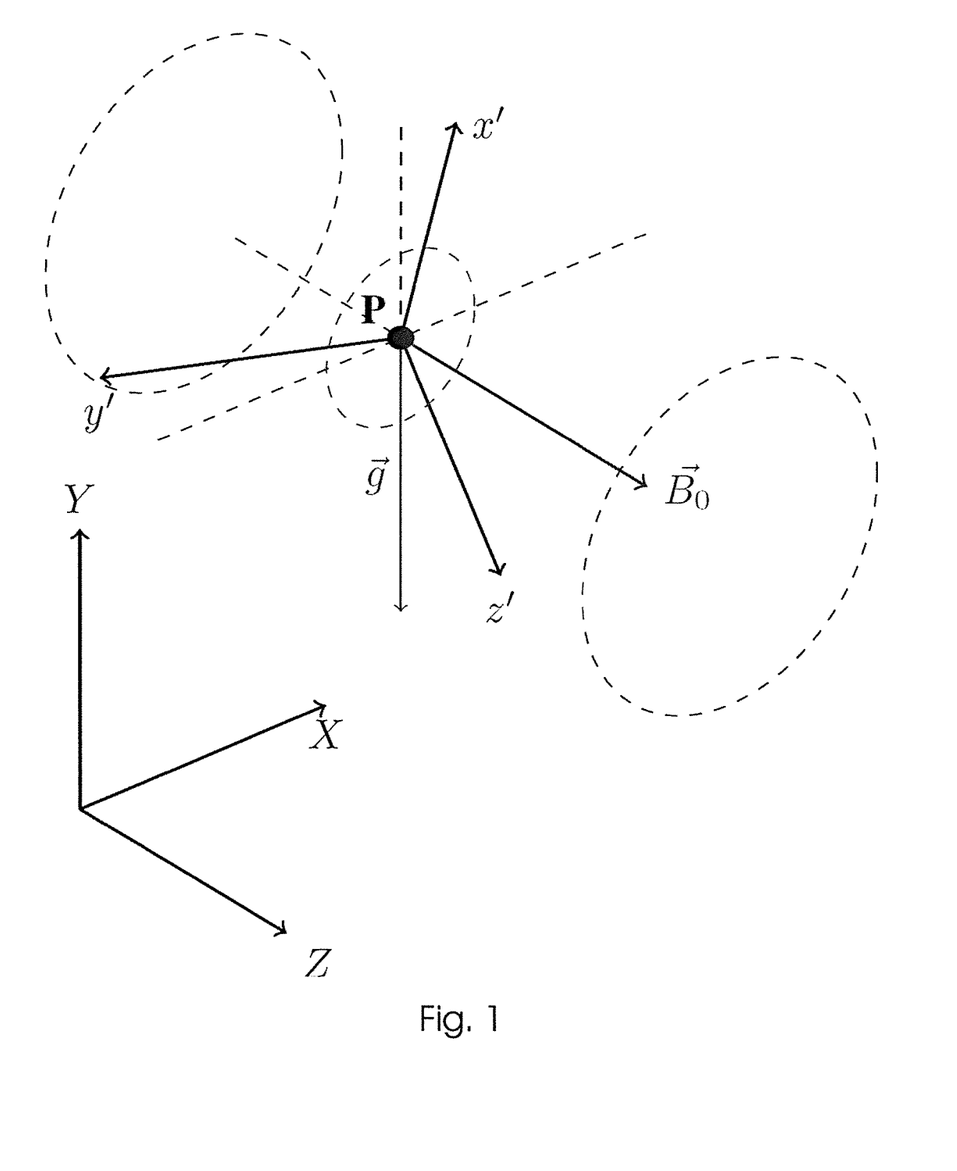
FIG. 1 describes a conventional MRI scanner layout in which gravity (~g) lies normal to the patient bed, and a static magnetic field (~B0) runs axially along the scanner bore.

FIG. 1 describes a conventional MRI scanner layout in which gravity (~g), which lies normal to the patient bed, and the static magnetic field (~B0), which runs axially along the scanner bore, are almost perfectly orthogonal to each other.

As part of the main magnet installation, as specified for the 3T Skyra used in this work, pendulums are used for aligning the scanner YZ plane to gravity.

A device (sensor) co-ordinate frame (x' y' z') is shown relative to the scanner co-ordinate frame (XYZ) and the large dotted circles represent the MRI scanner bore.

The ground lies parallel to the scanner XZ plane.

The vectors drawn represent the fields observable by the device at point P.

It will be appreciated that the use of two vector observations in the device frame allows for instantaneous measurements of orientation with respect to any reference frame in which the vector directions are known and is a intuitive method for showing the importance of orthogonality in reference vectors.

The two vectors also over-constrain the solution for a given transformation, this allows more freedom in synthesising the reference dataset as mentioned above. For instance, in most cases the magnetometer estimate will be more precise than the accelerometer measurement as it is independent of the dynamics of the system. In this case one can constrain the vector observation of gravity obtained from the accelerometer to only effect the output orientation about the axis of the static magnetic field. In another example, data with regards to the direction of gravity may be more easily obtained and the magnetometer output can be constrained appropriately.

It will be appreciated that the above mentioned synthesised reference dataset is beneficial in terms of ease of use of the device in that no scanner specific calibration is required if the synthesised estimates give sufficient accuracy for the application (which was found to be true for a prototype device in a standard clinical scanner 3T Skyra, Siemens). If the scanner's construction does however deviate considerably from these assumptions or higher accuracy (than the tolerances specified in the scanner's construction) are required one can perform a once-off calibration to measure the direction of the reference vectors (gravity and the static magnetic field) in the scanners imaging co-ordinate frame. Notice that it is not necessary to measure the direction of these vectors with the device itself, the scanner specific reference dataset would therefore be valid for any vector based orientation tracking device. Both the gravitational field and MRI scanner's static magnetic field vector directions are unlikely to deviate over the life of the scanner therefore this dataset is expected to be valid over an equally long period.

Thus the device 10 uses as a starting point magnetic reference data relating to the direction of the static magnetic field of the MRI scanner in a selected principle co-ordinate frame.

The direction of the earth's gravitational field in the principle co-ordinate frame is used as the second vector axis and so stored in the memory 12 is the earth gravitational reference data relating to the direction of the gravitational field of the earth in the selected principle co-ordinate frame.

The device 10 also includes a three axis accelerometer 14, a three axis magnetometer 16 and a three axis angular rate gyro 18. The function of these will be described in more detail below.

A communication module 20 communicates with the MRI scanner.

Although the primary application of the communication module 20 is to transfer data to the MRI scanner relating to the object's motion. It also serves as a means for the MRI scanner's control computer to synchronise events with the device or transmit, which portion of the pulse sequence is currently playing out, to the device. The ability to synchronise with the pulse sequence allows the digital controller to optimise filter parameters and reduce noise in measurements.

The communications module 20 also feeds back measurements from the accelerometer and/or gyroscope to the scanner for use to estimate future states of the device.

Integrating of the acceleration signals can yield a velocity/position estimates. The high temporal resolution state estimates may be combined with lower temporal resolution translation estimates computed by the scanner or reconstruction software by means of a filter to allow for more robust translation estimates.

A processor 22 is connected to the accelerometer 14, the magnetometer 16, the gyro 18 and communication module 20.

The processor 22 controls the operation of the device 10 by receiving and processing measurements from the accelerometer 14, the magnetometer 16 and the gyro 18 to calculate the orientation of the device 10 within the bore of the MRI scanner. This will be described in more detail below.

It will be appreciated that in the illustrated embodiment, the processor 22 and the other components are contained in a single housing which is connected to the body of the patient that is being scanned. In this preferred embodiment, the measurements from the various measurement modules are received and locally processed by the processor 22 before the results are transmitted from the device 10.

Thus, the orientation of the device 10 is calculated locally in the device.

However, in an alternative embodiment, it is possible to calculate the orientation of the device 10 remotely by transmitting the signals from the accelerometer 14, the magnetometer 16 and the gyro 18 to a processor located remotely, outside of the scanner bore using the communication module.

In this embodiment, the functionality of the illustrated processor 22 regarding calculating the orientation of the device will be shifted to the other processor which in combination will implement filtering of signals as well as the higher level calculations as described below.

In any event, in the preferred embodiment, the processor 22 uses the MRI scanner's static magnetic field reference data and earth gravitational field reference data to define a first set of reference axes as described above, thus enabling the device to output data in the selected reference co-ordinate frame.

It can be appreciated that the vector fields, gravity and ~B0, are both observable from any position within the imaging region of the scanner. There is also no limit on measurement range as all possible orientations are defined by the vector observations. In use, the device 10 is strapped or stuck (similarly to an ECG pad) to the patient, in any orientation or position, preferably selected such that the point of contact is not easily moved relative to the anatomy of interest during the scanning process. A common cause of spurious readings is skin movement where subcutaneous muscles can induce relative motion, in the case of brain imaging the mastoid process behind the ear would be an attractive site for sensor attachment. This is not possible with optical based motion tracking where line of sight is required.

Upon receiving from the magnetometer 16 a measurement of a magnetic field vector in the device (sensor) co-ordinate frame within the magnetic imaging scanner in which the orientation tracking device is placed in use (FIG. 3, Step 32), and receiving from the accelerometer 14 a measurement of an acceleration vector indicating the direction of the earth's gravitational field vector in the device (sensor) co-ordinate frame (FIG. 3, Step 34), the processor 22 uses the received magnetic field measurement and accelerometer measurement to calculate the orientation of the device with respect to a pre-determined principle co-ordinate frame.

The processor 22 does this by comparing the measured magnetic field vector with the stored static magnetic field of the magnetic imaging scanner and comparing the measured acceleration vector with the stored earth's gravitational field where the stored measurements are represented in the principle co-ordinate frame selected. FIG. 3, Step 36. In one example, these vectors can be synthesised as mentioned previously such that the selected principle frame is the MRI scanner's co-ordinate frame.

It will be appreciated that a measurement at any instant in time from the device 10 can be stored as an initial orientation measurement as the system will know it's orientation with respect to the selected reference co-ordinate frame at each sensor update. Any changes in orientation when strapped to the patient would represent an equal change in orientation of the object being tracked by the device.

Thus the processor 22 receives measurements periodically and uses these to determine the orientation of the device, additionally comparing the determined orientation of the device with a previously determined orientation of the device (in the case of an imaging scan the orientation of the device at the start of the scan) to determine if the orientation has changed and quantify the change in orientation with respect to the selected principle co-ordinate frame (which may be selected as the MRI scanner's imaging co-ordinate frame which is useful in the application of prospective motion correction).

At periodic intervals, the processor 22 receives further measurements from the magnetometer and accelerometer to determine the instantaneous orientation of the device. In one example embodiment the periodic intervals are milliseconds.

Thus it will be appreciated that the processor 22 receives further measurements from the accelerometer 14 and magnetometer 16 and uses these to determine the orientation of the device and wherein the processor 22 compares the determined orientation of the device with a previously determined and stored orientation of the device to quantify a change in orientation of a rigid object within the MRI scanner to which the device is attached, in use.

The processor 22 uses the time evolution of the sensor data to apply filtering techniques to mitigate the effects of spurious readings on the orientation estimate feedback to the scanner control unit.

It will be appreciated that a measurement of just acceleration is not equivalent to an observation of the earth's gravitational field vector as this can be unreliable and could result in spurious results (even though patients are not expected to undergo large continuous accelerations).

To address this, the above measurements can be complemented with an angular rate-gyro to accurately determine orientation during periods of linear acceleration. The resulting sensor array is known as a MARG sensing scheme (Magnetometer Accelerometer and Rate Gyro). This array of sensors is commonly used for orientation estimation in robotics and aviation. The proposed device differs in that it is used in a controlled environment with the exceptionally strong static magnetic field of the MRI scanner which is independent of motion. The result is the ability to precisely track gyro bias during acceleration and achieve precision well beyond conventional applications of similarly constructed orientation measurement devices.

The gyroscope thus allows for more robust filtering techniques in which the evolution of the device's orientation state is better defined.

The device 10 preferably also includes a battery 24 to power the other components of the device. The battery may be connected to the active components via a voltage regulator (not shown).

All of the components described above are incorporated into a printed circuit board.

In this regard, the high power gradient coils of a Magnetic Resonance Imaging (MRI) scanner can induce currents in conductive materials. These currents can in turn interact with the fields within the scanner causing undesirable effects. Long conductors within the scanner bore can also tune into the radio frequency (RF) fields and cause severe image artefacts. Most of these effects can be mitigated through careful printed circuit board layout minimizing conductive area and preventing resonance. For example all critical signal traces are kept as short as possible.

One can also shield the signal traces by keeping the outer layers of the PCB as ground planes and running sensitive signal traces only within the inner layers. This not only protects the signal traces from the high power transient magnetic fields but prevents the device itself from emitting RF energy that could show up as artefacts on the MRI image.

To further reduce any electromagnetic emissions, the processor 22 is implemented as a low power micro-controller clocked at a frequency suitably far from the Larmor frequency of the specific scanner.

The high strength static magnetic field is vulnerable to inhomogeneity caused by abrupt changes in magnetic susceptibility. In order to ensure that these effects are minimized, all components are specifically sourced to be MRI compatible. The device is kept as compact as possible and supports its own power supply. The use of a battery frees up the device from long conductors that require shielding or extra protection.

The orientation estimates obtained by the device are transmitted by the communication module out of the scanner using either optical or wireless communication technologies (in the form of electro-magnetic waves that are suitably far from the precession frequency of the MRI scanner), ensuring that no long conductors are required.

Using modern digital sensors makes the sensor analogue signals less susceptible to radio frequency flux due to the minute size of the internal structures of the Integrated Circuits (ICs). These signals are immediately digitised after being low pass filtered within the silica structure of the integrated circuit reducing the chances of signal coupling to the transient magnetic fields.

Analogue and digital power supplies are separated and a low pass filter is used at close proximity to the sensor IC supply pins to reduce the effects of induced currents caused by the high power gradient coils.

Two separate algorithms have been proposed to obtain the desired filter outputs.

Firstly, a popular filter implemented in orientation estimates for body tracking and small aircraft can be adapted for use on the device. This filter is a light weight quaternion based version of a complementary filter initially described by Mahony. This filter has comparable performance to Kalman filters at a much smaller computational cost. An example implementation of the explicit complementary filter proposed by Mahony is described in FIG. 4. The compensation block, top right, is a modified version of a technique initially introduced by Madgwick for magnetic field compensation. In this case the compensation block is used to mitigate the effects of spurious accelerations in the same direction as the static magnetic field. This also allows a less restrictive constraint if an a priori estimate of the direction of the earth's gravitational field is used as a vector reference because the acceleration vector is now constrained to only effect orientation about the axis of the static magnetic field of the MRI scanner.

Figure 4:
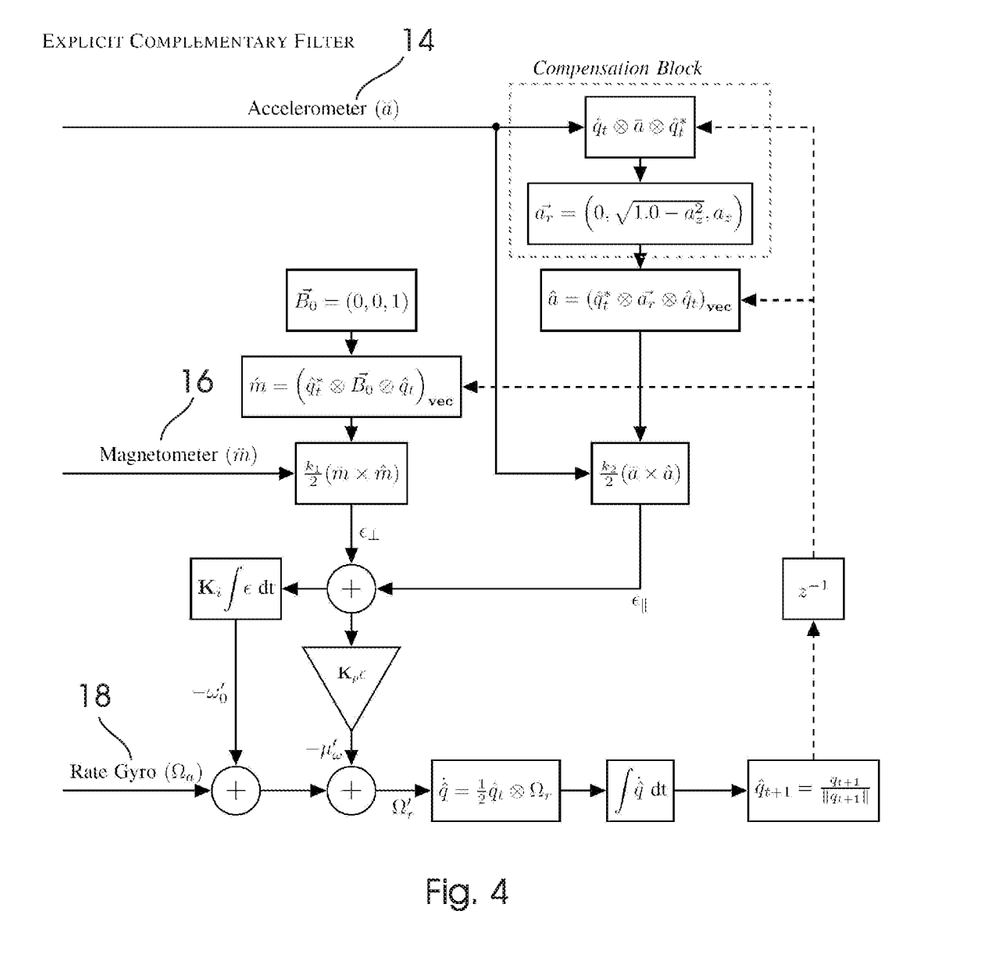
FIG. 4 shows an example non-linear complementary filter.

In the example implementation shown in FIG. 4 an a priori reference vector set is used where the static magnetic field vector is assumed to be perfectly parallel with the scanner co-ordinate frame Z-axis (normal to the transverse plane) and the gravitational vector field is assumed to lie on the YZ-plane (the sagittal plane) of the scanner frame (descriptions are for a patient in the headfirst supine position, in the standard MRI scanner layout mentioned above). The proposed filter therefore outputs orientation in the MRI scanner's co-ordiante frame.

The second filter solution, which can be applied in an embodiment absent of angular rate gyro measurements, proposes the use of an algorithm designed for spacecraft attitude estimation and is a streamlined least squares solution to Wahba's problem:

$$F_{min}\left(\frac{1}{2}\sum_i a_i |\vec{b_i} - R\vec{r_i}|^2\right)$$

Where:
ai=A vector weighting coefficient, which can be related to variance for a maximum likelihood estimate.
bi=ith vector observation in the patient frame.
ri=ith vector observation in the reference frame.
R=optimal rotation.

The algorithm implemented to solve the above equation is known as the EStimator of the Optimal Quaternion (ESOQ2) and was proposed by Markley. The above-mentioned technique is useful when there is reference data available for both the direction of gravity and the static magnetic field in the imaging frame. Put simply, when the orientation solution is over-constrained. In this case the filter would optimally combine the two sensor estimates. It is expected that the magnetometer observations would be more highly weighted in this case due to the small variance and the motion independence of this vector observation. This filter wouldn't improve the performance of the linearly independent components of each vector as the magnetometer measurement gives no information about the orientation with respect to the axis of the static magnetic field and the accelerometer measurement gives no information about the orientation with respect to the axis of the earth's gravitational field. Patient acceleration would therefore be directly visible on the orientation output about the axis of the scanners static magnetic field.

The first implementation is largely independent of linear accelerations and relies on the integration of the angular rate gyros for the orientation estimate. The first method is therefore better suited to dealing with effects of the MRI scanners magnetic fields on the acceleration sensor. The second relies solely on the acceleration and magnetic field vectors as inputs and is therefore inherently more vulnerable.

Both algorithms outputted data that was stable to within 0.01 degrees about the axis of the ~B0 field and to within 0.006 degrees about the pair of orthogonal axes lying on the plane perpendicular to the ~B0 field. As is expected the implementations including angular rate data achieve better performance during gradient intensive scanning (such as diffusion tensor imaging) where scanner bed vibrations introduce noise into the accelerometer output.

In any event, it will be appreciated that combining vector observations with an angular rate measurement efficiently is advantageous for reliability of the orientation estimates computed by the device. The process of computing orientation in either of the methods is relatively lightweight allowing for low latency transmission of motion parameters (<1 ms in the current prototype on a low power microcontroller clocked at 32 MHz). The close relationship between the vectors and orientation means when using the device presented the orientation data more accurately represents the motion of the patient in real-time than most (all to the inventors knowledge) existing technologies for external motion correction in MRI.

Figure 5:
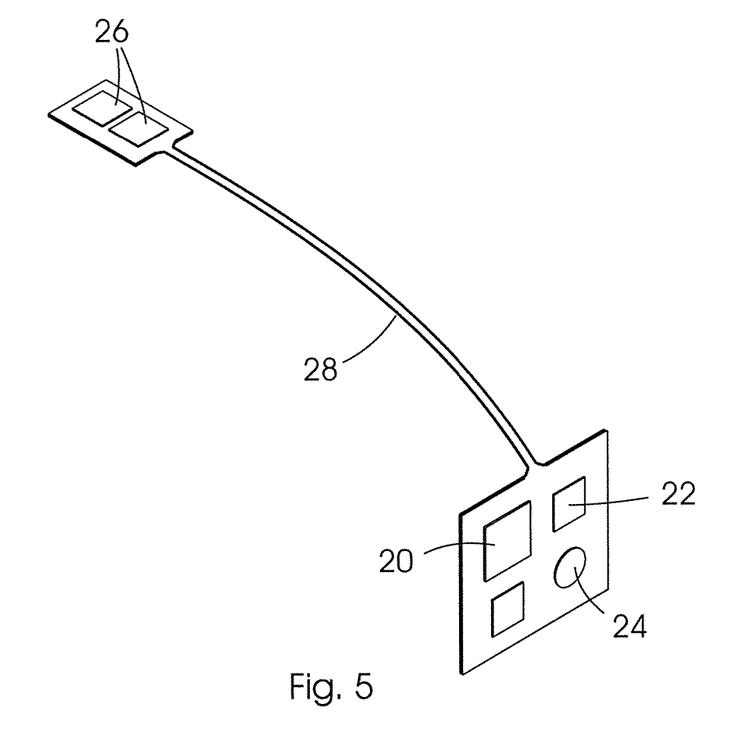
FIG. 5 is an example user wearable device incorporating the orientation tracking device of the present invention.

FIG. 5 shows one example embodiment of a user wearable device including the orientation tracking device described above.

The device includes a sensor mount attachment 26 to which the accelerometer 14, magnetometer 16 and gyro 18 can be attached.

This attachment 26 can be made very small and is the part that is rigidly constrained to the anatomy of interest.

A very flexible cable 28 is used for carrying power and provides a digital communication link.

The processor 22, communication module 20 and battery 24 are then located away from the sensor mount attachment 26.

The advantage of this layout is the small size of the layout and additionally that the non-sensing components have been physically distanced from the sensors and thereby do not interfere with the sensors. It is also desirable in that it reduces the risk of patient discomfort.

In any event, it will be appreciated that the technology proposed is an MRI compatible device capable of measuring vectors within the scanner bore.

The device is also capable of transmitting and receiving data through the communication module with the MRI scanner. The proposed vector observations are ideally suited, but not limited to, orientation estimates.

In trials, the prototyped technology has so far overcome many of the disadvantages of current orientation observation techniques.

The current prototype is capable of precisely estimating the orientation of an object within the MRI scanner bore at a high temporal resolution (every ms) and accuracy (within a tenth of a degree), independently of the MRI pulse sequence. The technology is not restricted or unique to any specific pulse sequence and is therefore very versatile.

It was also found that with a prototype device sufficient resolution of the subject's orientation was achieved to view involuntary motion such as the cardiac and respiration cycles.

Figure 6:
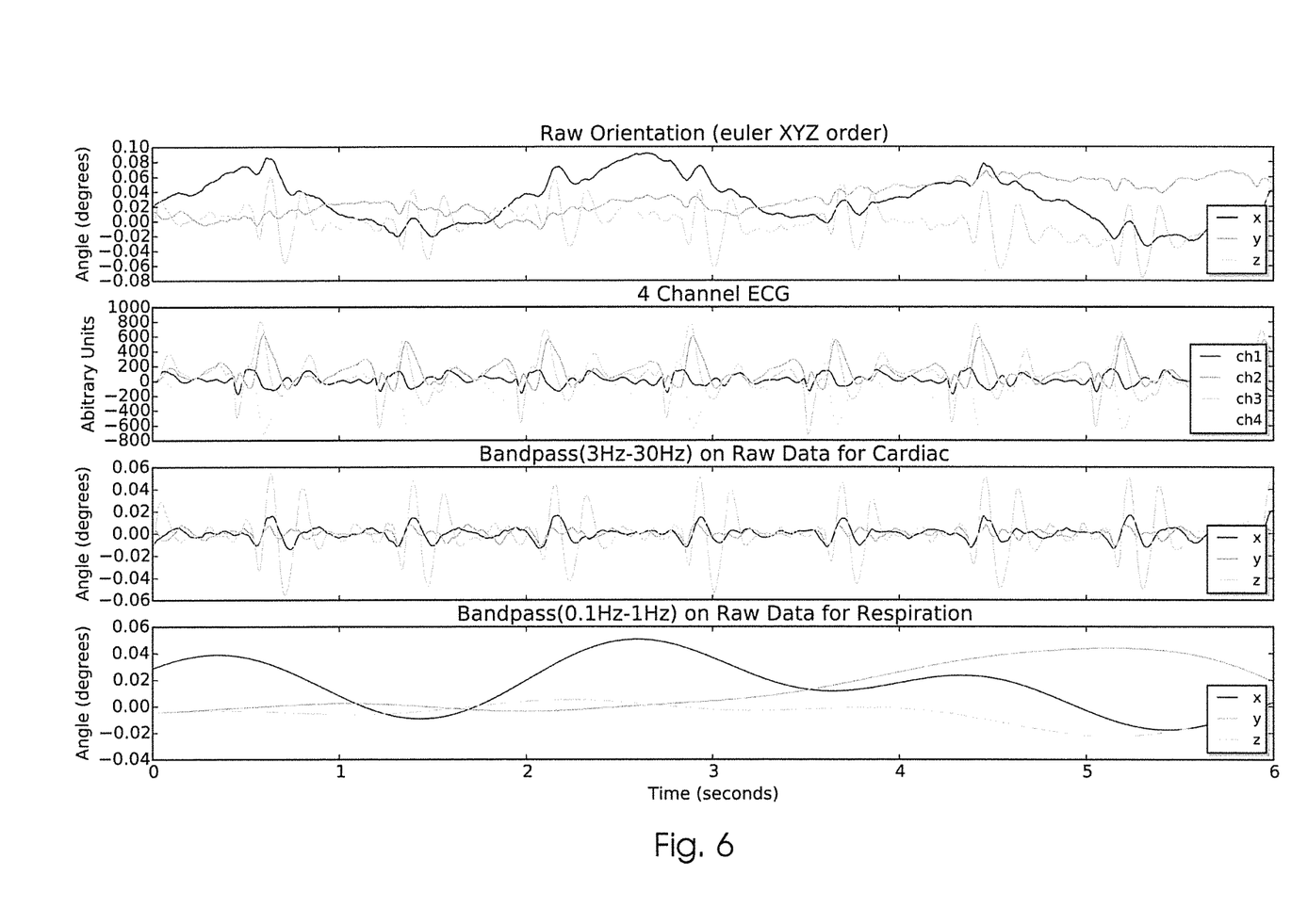
FIG. 6 shows graphs comparing cardiac and respiration data derived from the sensor with direct ECG and respiration measurements.

Referring to FIG. 6 the raw data in all 3 axes showed a strong relationship to a 4 channel electro-cardiogram (ECG) signal obtained while a subject lay motionless within the MRI scanner.

The orientation measurement is made relative to the scanner's static magnetic field and the earth's gravitational field. These fields lie almost perfectly orthogonal in conventional MRI scanner layouts reducing the noise in orientation estimates, making the MRI environment ideal for this measurement technique. Due to the way in which a MRI scanner is constructed the current prototype has shown sufficient precision for prospective motion correction in MRI without any scanner specific calibration in the example scanner used.

The technology gives one the ability to detect and quantify rigid body rotations and feed them back to the MRI scanner in real time to reduce the effects of motion on image quality. The measurements can be used to optimise current navigator techniques or even be implemented in conjunction with current external 3D translation tracking techniques for complete rigid body motion correction.

Figure 7:
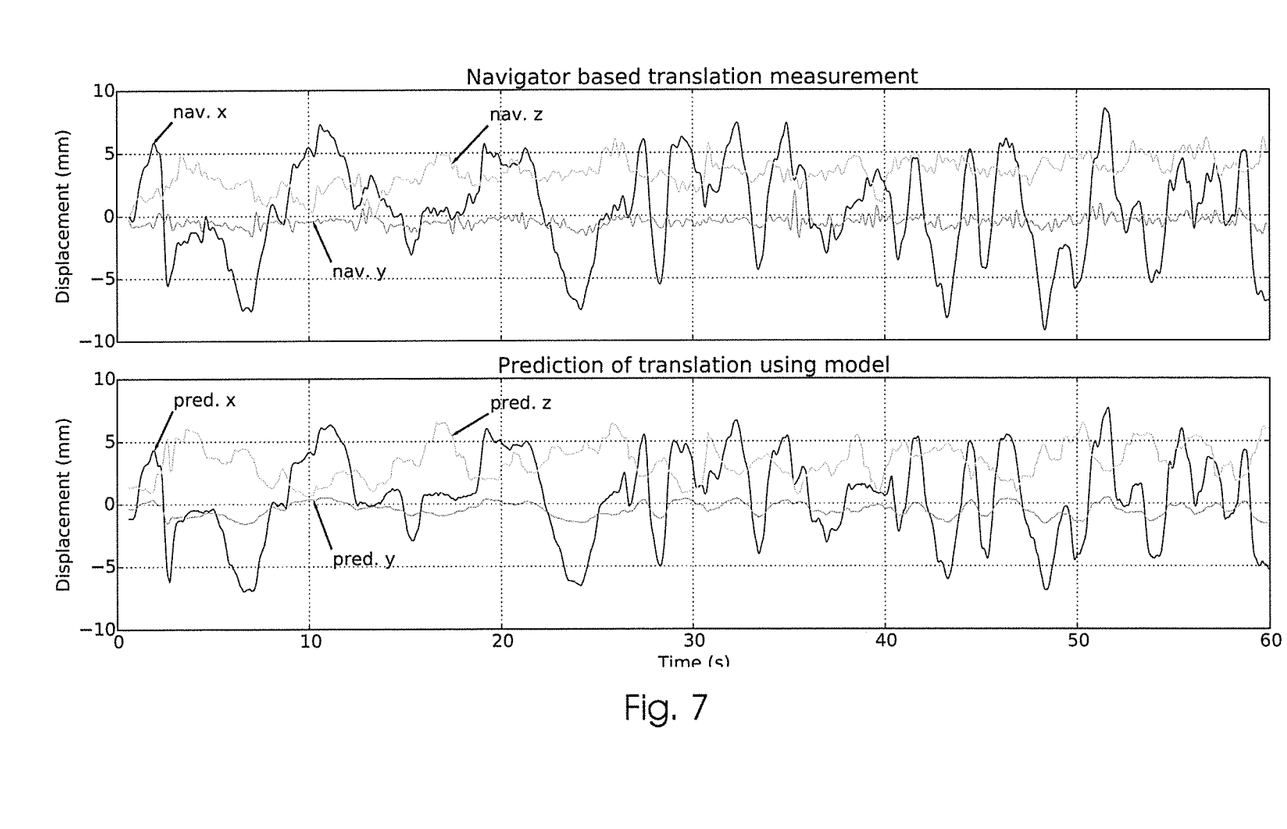
FIG. 7 shows graphs comparing translation data from a linear navigator compared to translation data using the orientation obtained from the orientation tracking device.

In the application of neuro/brain imaging the orientation outputs of the device can be used to predict translation as these quantities are closely correlated to change in orientation. FIG. 7 shows an example dataset of the application of using the device to predict translation compared to navigator based data for the same motion. The effects of translational motion (in the case of FIG. 7 severe motion) on image quality can be greatly reduced by applying the results of this model.

Figure 8:
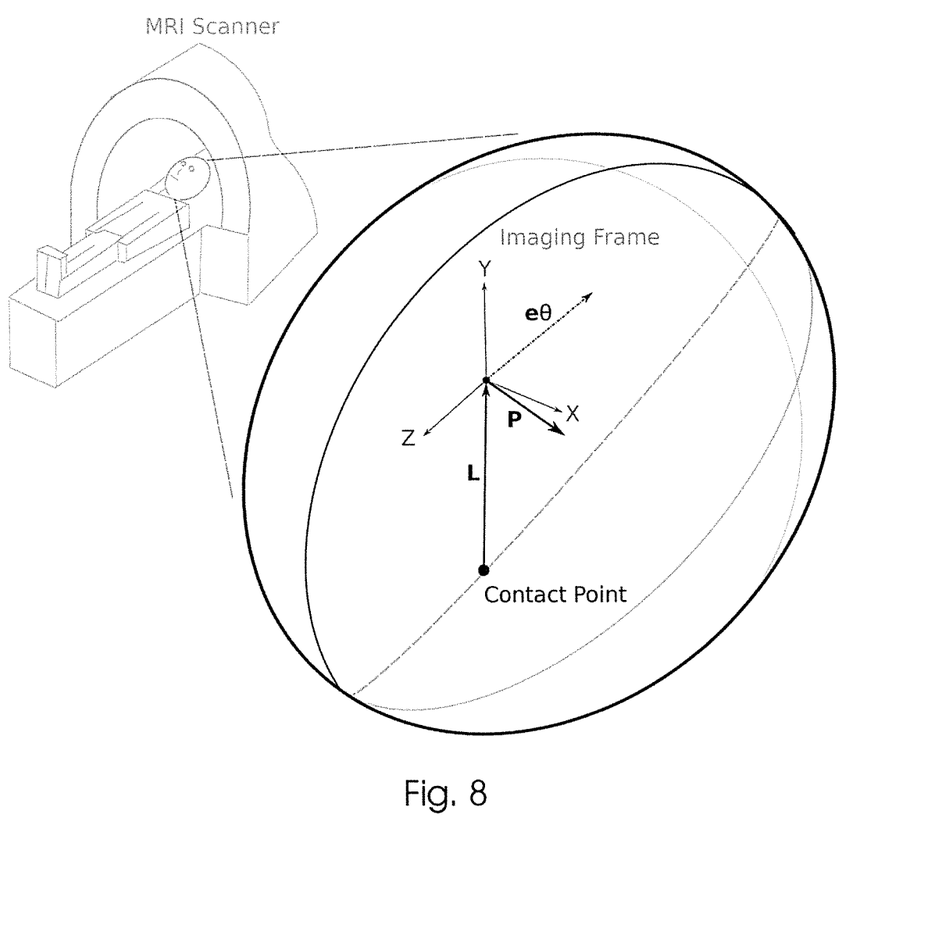
FIG. 8 shows a graphical representation of the rolling model used to predict the motion plotted in FIG. 7.

FIG. 8 shows the vectors used to relate translation to orientation in the simplified model presented. The predicted translation shown is simply the result of the vector cross product of the axis-angle vector and an estimate of the initial position vector between the gradient iso-center and the point at which the patient's head makes contact with the scanner bed.

$$\vec{P} = \theta(\vec{e} \times \vec{L})$$

Where:

$\vec{P}$ is the predicted translation of the imaging frame.

$\theta$ is the magnitude of the angle rotated.

$\vec{e}$ is the unit magnitude axis of rotation.

$\vec{L}$ is the initial offset vector pointing from the patient's initial point of contact with the scanner bed and the origin of the field of view.

The above equation is as a result of a highly simplified model relating to the assumption of rolling motion and small angles. It is therefore most accurate if no slipping happens between the patients head and scanner bed. The vector $\vec{L}$ (initial displacement) will generally have a constant vertical component and is expected to be invariant with respect to different patients.

In any case, it can be appreciated that the device can be used to perform full rigid body motion correction at a high temporal resolution using a model to predict translation that isn't dependent on skull geometry or patient specific characteristics over small angles.

In another application the translation measurement from the model presented above can be compared to a measurement of translation from another source (navigator, active marker etc.) to predict if sensor detachment has occurred. Sensor detachment is when the mounting of the device to the anatomy of interest is disturbed, which can cause substantial image artefacts). If the model output and translation measurement have a strong discontinuity one can expect that the device moved relative to the anatomy of interest. At detection of an event the device can store a new reference and continue tracking motion relative to the new reference. The change in orientation relative to the new reference is then applied relative to the last valid orientation measured with the old reference. Even though sensor detachment is less likely to occur with the versatility in mounting of the described device this is an effective way of minimizing the effects of a known challenge in external motion tracking methods.

The technology could be seen as a gateway to optimal real time motion correction in MRI scanners, reducing the complexity of motion detection due to the knowledge of a reliable orientation estimate. Other uses include respiration gating, cardiac gating and eddy current detection.

The device can be used to alert the patient or doctor to movement, prompting patient adjustment or a re-scan. However, the main application is that the orientation information generated by this device can be fed into MRI scanners to correct in real time for scanning error caused by movement of the patient. This will ultimately improve the image quality produced, whilst minimising or preventing wasted time needed for rescanning The final implementation of the technology can thus reduce scan times, improving efficiency of clinical MRI scanners, saving hospitals and patients money. The technology can be used to reduce artefacts in 'hard to scan' subjects and reduce scan times for the ill, elderly and very young. Motion correction is especially important for special contrast modularities such as functional MRI and diffusion imaging and can improve the statistical significance of research results.

In contrast to other known external motion correction techniques in magnetic resonance imaging, which require three position estimates for orientation detection, the disclosed invention uses vector observations from a single point in space. The result is that miniaturization of the device is only restricted by miniaturization of current semi-conductor technology. This is advantageous for patient comfort, reduction in interactions with the highly sensitive static magnetic field and lastly minimization of induced torques on the conductive materials used in circuit design.

The results obtained from the current prototype have proven the compatibility of some existing semi-conductor technologies with the harsh MRI environment. The results are not only precise, but also robust. The device simplifies the problem of motion correction within MRI scanners by addressing many of the problems associated with current techniques such as cost, size, accuracy and most importantly ease of use.

The invention claimed is:

1. An orientation tracking device, the device including:
   a memory for storing data therein including magnetic reference data relating to the direction of a static magnetic field of a magnetic imaging scanner in a selected principle co-ordinate frame and earth gravitational reference data relating to the direction of the gravitational field of the earth in the principle co-ordinate frame;
   an accelerometer;
   a magnetometer;
   a communication module; and
   a processor connected to the accelerometer, the magnetometer and communication module, the processor adapted for:
      receiving from the magnetometer a measurement of a magnetic field vector in a co-ordinate frame of the orientation tracking device, within the magnetic imaging scanner in which the orientation tracking device is placed in use;
      receiving from the accelerometer a measurement of an acceleration vector in the orientation tracking device's co-ordinate frame, within the magnetic imaging scanner in which the orientation tracking device is placed in use; and
      determining the orientation of the device with respect to the principle co-ordinate frame by comparing the measured vectors from the accelerometer and magnetometer with the stored gravitational reference data and magnetic reference data respectively.

2. A device according to claim 1 wherein the processor receives further measurements from the accelerometer and magnetometer and uses these to determine the orientation of the device.

3. A device according to claim 2 wherein the processor compares the determined orientation of the device with a previously determined orientation of the device to quantify a change in orientation of a rigid object within the MRI scanner to which the device is attached, in use.

4. A device according to claim 1 wherein the processor further applies filtering techniques to mitigate the effects of spurious readings.

5. A device according to claim 1 wherein the device includes at least one gyroscope also connected to the processor, so that the processor additionally uses measurements received from the gyroscope to determine orientation of the device.

6. A device according to claim 5 wherein the communication module further feeds back acceleration and/or gyroscope measurements to the scanner for use to estimate future states of the device.

7. A method of using an orientation tracking device to track orientation, the method including:
   storing data including magnetic reference data relating to the direction of a static magnetic field of a magnetic imaging scanner in a selected principle co-ordinate frame and earth gravitational reference data relating to the direction of the gravitational field of the earth in the principle co-ordinate frame;
   receiving from a magnetometer a measurement of a magnetic field vector in a co-ordinate frame of the orientation tracking device, within the magnetic imaging scanner in which the orientation tracking device is placed in use;
   receiving from an accelerometer a measurement of an acceleration vector in the orientation tracking device's co-ordinate frame within the magnetic imaging scanner in which the orientation tracking device is placed in use; and
   determining the orientation of the device with respect to the principle co-ordinate frame by comparing the measured vectors from the accelerometer and magnetometer with the stored gravitational reference data and magnetic reference data respectively.

8. A method according to claim 7 wherein measurements are received periodically and used to determine the orientation of the device.

9. A method according to claim 8 wherein the determined orientation of the device is compared with a previously determined orientation of the device to quantify a change in orientation of a rigid object within the MRI scanner to which the device is attached, in use.

10. A method according to claim 7 wherein filtering techniques are applied to mitigate the effects of spurious readings.

11. A method according to claim 8 further including receiving measurements from at least one gyroscope and additionally using the measurements received from the gyroscope to determine orientation of the device.

12. A method according to claim 11 further including feeding back acceleration and/or gyroscope measurements to the scanner for use to estimate future states of the device.

13. A method according to claim 7 in which the principle co-ordinate frame is the co-ordinate frame of the MRI scanner.

14. A method according to claim 13 in which the reference data is synthesised based on knowledge of the MRI scanner construction.

15. A method according to claim 7 in which a change in orientation of a rigid object to which the device is connected in use is used to predict the translation of that object.

* * * * *